United States Patent [19]

Cadmus et al.

[11] 4,394,447

[45] Jul. 19, 1983

[54] PRODUCTION OF HIGH-PYRUVATE XANTHAN GUM ON SYNTHETIC MEDIUM

[75] Inventors: Martin C. Cadmus; Clarence A. Knutson, Jr., both of Peoria, Ill.

[73] Assignee: The United States of America as represented by the Secretary of Agriculture, Washington, D.C.

[21] Appl. No.: 908,601

[22] Filed: May 23, 1978

[51] Int. Cl.³ .................... C12P 19/06; C12P 19/04; C12R 1/64

[52] U.S. Cl. .................................... 435/104; 435/101; 435/910; 426/658

[58] Field of Search ...................... 195/31 P, 96, 100; 435/101, 104, 910; 426/658

[56] References Cited

U.S. PATENT DOCUMENTS

| | | | |
|---|---|---|---|
| 3,054,689 | 9/1962 | Jeanes et al. | 106/208 |
| 3,391,060 | 7/1968 | McNeely | 195/31 P |
| 3,438,865 | 4/1969 | Work et al. | 195/96 |
| 3,565,763 | 2/1971 | Cadmus et al. | 195/31 P |
| 3,594,280 | 7/1971 | Collin et al. | 195/31 P |
| 3,671,398 | 6/1972 | Collin et al. | 195/31 P |
| 4,119,546 | 10/1978 | Wernau | 195/31 P X |
| 4,154,654 | 5/1979 | Campagne | 435/104 |

FOREIGN PATENT DOCUMENTS 2708239 9/1977 Fed. Rep. of Germany .... 195/31 P

OTHER PUBLICATIONS

Sandford et al., "Variation in *Xanthomonas campestris* NRRL B-1459 Characterization of Xanthom Products of Differing Pyruvic Acid Content" *Exracellular Microbial Polysaccharides*, A.C.S. Symposium Series 45 A.C.S., Washington, (1977) Sandford et al. ed. pp. 192-209.

Cadmus, et al., "Colonial Variation in *Xanthomonas campestris* NRRL B-1459 and Characterization of the Poly Saccharide from a Variant Strain", *Can J. Microbiol.*, vol. 22, (1976), pp. 942-948.

Jeanes et al., USDA ARS-NC-51 (Nov. 1976), pp. 10-11.

Cadmus et al., Abstract No. 29 (CSCE), Abstracts of Papers, The Chemical Institute of Canada and A.C.S. Joint Conference, May 29-Jun. 2, 1977.

Moraine et al., "Kinetics of the Xanthan Fermentation", *Biotechnology and Bioengineering*, vol. XV, (1973), pp. 225-237.

*Primary Examiner*—Thomas G. Wiseman
*Attorney, Agent, or Firm*—M. Howard Silverstein; David G. McConnell; Curtis P. Ribando

[57] ABSTRACT

A high-pyruvate xanthan gum, substantially free of insolubles and undesirable coloration, is produced by fermentation of *Xanthomonas campestris* on a carbohydrate-containing nutrient medium having $(NH_4)_2HPO_4$ at a level of at least 0.15% as the primary nitrogen source, and having a total phosphate level of at least about 0.25%.

3 Claims, No Drawings

PRODUCTION OF HIGH-PYRUVATE XANTHAN GUM ON SYNTHETIC MEDIUM

BACKGROUND OF THE INVENTION

1. Field of the Invention

This invention relates to the production of high-pyruvate xanthan gum by culturing *Xanthomonas campestris* on a novel synthetic growth medium.

2. Description of the Prior Art

Xanthan gum is a heteropolysacchride produced as a fermentation product by *X. campestris*. Its structure consists of $\beta$-(1→4)-linked D-glucosyl backbone chain with alternate residues having appended thereon a three-unit side chain of D-mannose and D-glucuronic acid in the molar ratio of 2:1. Half of the side chain D-mannosyl residues are attached directly to the main chain through $\alpha$-(1→3) linkages. The remaining D-mannosyl residues occur as nonreducing end groups. Approximately half of these D-mannosyl groups carry pyruvic acid as the di-O-4,6-ketal.

Although *X. campestris* is not difficult to cultivate on standard laboratory media, certain strain variations have been observed, both in continuous and batch-type fermentations, which affect the quality and yield of the gum. Variation was first associated with the formation of large (L) and small (S) colony types [M. C. Camus et al., Can. J. Microbiol. 22: 943 (1976)], herein incorporated by reference. The L-type produced high yields of the heteropolysacchride with apparently normal rheological characteristics, while the S-type gave low yields with undesirable properties. The only detectable structural difference was a significantly lower pyruvate concentration in the S-type polysaccharide. It was subsequently shown in greater detail (P. A. Sandford et al., Polysaccharides of Industrial Importance Symposium, 172nd Meeting, American Chemical Society, August 29-September 3, 1976) that viscosities of dilute (0.5% or less), aqueous, xanthan solutions are directly related to the pyruvic acid content of the gum. In fact, it appears that the pyruvic acid content is the best indicator of polysaccharide quality.

Xanthan gum is produced in both the United States and Europe, and has numerous applications in food and nonfood industries. Many of these applications require a quality product having a pyruvic acid content above about 3.3% by weight and being substantially free of insoluble material and/or color. Most product methods, such as those disclosed in U.S. Pat. Nos. 3,054,689, 3,594,280, and 3,671,398 use an organic nitrogen source (e.g., dried distillers' solubles) in a carbohydrate-containing nutrient medium. Thes organic materials are disadvantageous in that they are not always readily available, they sometimes fail to stimulate production of high-pyruvate polysacchrides, and they reduce the gum quality by virtue of their residual insolubles and dark coloration. The requisite purification procedures for obtaining an acceptable product from these gums are quite elaborate and costly.

An attempt to overcome the problem of the insolubles is taught in U.S. Pat. No. 3,391,060, wherein inorganic ammonium nitrate is substituted for the organic nitrogen nutrient. Although this approach was somewhat successful, both polysaccharide yields and pyruvate content were undesirably low. Another inorganic nitrogen source, diammonium phosphate, has been utilized in U.S. Pat. No. 3,438,865 as a nutrient for *Escherichia coli* in the production of lipopolysaccharides. However, its usefulness in culturing *X. campestris* has not been previously taught.

SUMMARY OF THE INVENTION

We have now unexpectedly discovered that when diammonium phosphate at a level of at least 0.15% (g./100 ml.) is used as the primary nitrogen source in the fermentation of a carbohydrate-containing nutrient medium with *X. campestris* and when the total phosphate level is at least about 0.25%, the xanthan gum produced by the microorganisms is not only substantially free of insolubles and undesirable coloration, but also is characterized by a high pyruvic acid content.

In accordance with this discovery, it is an object of the invention to obtain a high yield of a high-pyruvate xanthan gum from fermentation of a nutrient medium with *X. campestris*.

It is also an object of the invention to simplify the recovery of xanthan gum from the nutrient medium.

Another object of the invention is to produce a xanthan gum which imparts high viscosities to dilute solutions thereof.

Other objects and advantages of this invention will become readily apparent from the ensuing description.

DETAILED DESCRIPTION OF THE INVENTION

This invention is applicable to the bacterium *X. campestris*, including all strains, substrains, and other variants thereof. This bacterium has been widely used in the prior art for the production of xanthan gum and its morphological characteristics are well known. *X. campestris* NRRL B-1459 is exemplary of the useful strains, though other known strains would be substantially equivalent for purposes of this invention. Of course it is understood that there will be some variability of gum yield and pyruvic acid content among the variants. For purposes of this invention, the terms "gum" and "polysaccharide" are used interchangeably, and "high pyruvate" is defined herein as having a pyruvic acid content of 3.3% by weight or more.

The basic carbohydrate-containing nutrient medium for use in this invention is essentially the same as those conventionally used for culturing *X. campestris*, but substantially without the organic nitrogen source. Typically, these media are tap water solutions containing 1-5% of a suitable carbohydrate source, such as D-glucose, fructose, maltose, sucrose, starch, and the like. For most purposes, D-glucose is preferred at a level of about 2.5%. Magnesium ions are generally supplied by the addition of a salt, such as $MgSO_4$ at a level of about 0.01% of the solution.

For optimum growth, it is desirable to maintain the pH between about 6.8 and 7.5, though satisfactory results may be obtained as low as pH 5.5. As the fermentation proceeds, the pH tends to drop. This can be controlled by the addition of base, such as KOH, NaOH, or $NH_4OH$ during the course of the reaction. Alternatively, an alkali buffer can be added to the starting broth. Preferred buffers are $K_2HPO_4$ and $Na_2HPO_4$.

In accordance with the invention, the primary nitrogen source to be included in the nutrient medium is diammonium phosphate, $(NH_4)_2HPO_4$. By "primary nitrogen source" it is meant that its level relative to the levels of other nitrogen sources which may be in the medium is such that the other sources have substantially no effect on the pyruvate content of the polysaccharide.

In order to obtain high-pyruvate polysaccharides, it is critical that the diammonium phosphate level in the medium be at least about 0.15% (g./100 ml.), and the total phosphate level be at least about 0.25%. Any phosphate deficit can be made up by the addition of either the $Na_2HPO_4$ or $K_2HPO_4$ buffer or an equivalent phosphate source. As the ammonium phosphate levels are increased about 0.15%, the pyruvate content is also increased, and the pyruvate peaks at ammonium phosphate levels of 0.25-0.35%. Beyond 0.35%, there is substantially no effect on either pyruvate or yield. The combination of 0.15-0.25% $(NH_4)_2HPO_4$ and 0.25% additional phosphate appears to be optimum for production of high-pyruvate polysacchrides in high yields.

In practice of the invention, the novel carbohydrate-containing medium with the diammonium phosphate is inoculated with *X. campestris* previously cultured on an inoculum broth containing an organic nitrogen source. An inoculum size of 5-15% (v/v) is suitable, though below 7.5% there may be a lag in initial growth resulting in longer fermentation times and lower yields. At these inoculum levels, the amount of organic nitrogen which is transferred with the broth to the medium is sufficiently insignificant such that it neither has any substantial effect on the pyruvate content of the polysaccharide, nor does it contribute significantly to the color and insolubles content of the final fermentation medium. Incubation is conducted at temperatures in the range of 21°-29° C. for about 3 days or until all of the carbohydrate is utilized. At 21° C., the pyruvate content is highest, though the growth rate and polysaccharide yields are retarded. At 29° C., growth rate and yields are accelerated slightly, but there is some reduction in pyruvate content. Preferred temperatures are in the range of 27°-28° C.

Another factor affecting the quality of the gum is the method used to sterilize the medium. Heat sterilization of the salts prior to aseptic addition to the fermentors results in approximately an 11% increase in pyruvic acid over filter sterilization wherein the salts are passed through a sterilized filter membrane. Filter sterilization removes some insoluble matter (salts) which is apparently beneficial for the quality of the product.

The aeration rate also influences the quality of the polysaccharide. For 10-l. fermentations in 20-l. fermentors, maximum pyruvate is realized at an air-flow rate in the range of about 0.75 vol./l./min. to about 1.5 vol./l./min., though the operable limits range from 0.25-1.5 vol./l./min. At the higher levels, growth rates may be accelerated, thereby reducing the fermentation time to 2 days.

The polysacharide is recovered from the whole culture fluid by any known procedure which separates the residual solids from the gum suspension. Effective results can be obtained by centrifuging for about 30 min. at 20,000 r.p.m. in an ultracentrifuge. The gum can then be precipitated with ethanol in the presence of a salt such as potassium chloride. It is then filtered, washed, and dried by any procedure as known in the art.

The gums produced by this process have viscosities of about 800 centipoises (cp.) at the 0.5% level in distilled water at room temperature. By addition of 1.0% KCl, the viscosity can be increased to about 1900 cp. Pyruvate contents range from about 3.3 to about 4.4% by weight of the gum and yields are in the range of from about 0.9 to about 1.4 g. of gum per 100 ml. of culture broth. Actual properties are of course dependent upon the particular substrain of *X. campestris* and the conditions of fermentation. These polysaccharides may be used for all purposes conventionally employing xanthan gum. They are particularly useful as solution thickeners where it is desirable to minimize both the amount added and the discoloration of the solution.

The following examples are intended only to further illustrate the invention and are not intended to limit the scope of the invention which is defined by the claims.

EXAMPLE 1

Substrains of *X. campestris* NRRL B-1459 for use in the succeeding examples were propagated and maintained by the following procedure.

Yeast-malt broth tubes were inoculated from lypohile cultures of NRRL B-1459 and shaken for 24 hours at 25°-28° C. The broth cultures were transferred onto yeast-malt agar slants, incubated for 24 hours at 25° C., and stored at 4° C. as stock cultures. During the course of maintenance, these stock cultures were streaked on yeast-malt agar plates and incubated for 3 days at 25°-28° C. to check for colony size. When variant substrains were identified, they were put on stock cultures and maintained. These substrains were also lyophilized and deposited in the Northern Regional Research Laboratory Culture Collection in Peoria, Illinois, and assigned the deposit numbers shown in Table I. NRRL B-1459-S-29 was virtually identical to B-1459A except that it was maintained for several months on tryptone-glucose-yeast agar. The stock culture of NRRL B-1459-4L (old) was approximately 1 year old.

Except for B-1459A, all substrains were tested for xanthan production by culturing on the following productivity medium adjusted to pH 7.0 following the procedure reported in Cadmus et al. [Can. J. Microbiol. 22: 943 (1976)], supra.

| | |
|---|---|
| D-glucose | 2.1% |
| distillers' dried solubles | 0.8% |
| $K_2HPO_4$ | 0.5% |
| $MgSO_4$ | 0.01% |
| tap water | 96.59% |
| | 100.00% |

EXAMPLES 2-8

Fresh cultures were prepared by inoculating yeast-malt agar slants from the stock cultures of certain substrains reported in Table I. These slants were incubated for 20 to 24 hours at 25° C., and then the bacterial cells from the slants were suspended in 7 ml. of sterile yeast-malt broth. Inoculum buildup was carried forward in three stages. In the first stage, 1 ml. of broth containing the fresh cells was inoculated into 50 ml. broth in 300-ml. Erlenmeyer flasks and then incubated on a rotary shaker (200 r.p.m.) for 22 hours at 27° to 28° C. In the second stage, 50 ml. (10% v/v) of the first stage cultures were transferred to Fernbach flasks containing 500 ml. of broth at pH 7 comprising:

| | |
|---|---|
| D-glucose | 1.2% |
| yeast extract | 0.15% |
| malt extract | 0.15% |
| peptone | 0.25% |
| $(NH_4)_2HPO_4$ | 0.15% |
| $K_2HPO_4$ | 0.25% |
| $MgSO_4$ (anhydrous) | 0.005% |
| tap water | 97.845% |

-continued 100.000%

The cultures were incubated on a rotary shaker (200 r.p.m.) for 22 hours. The final stage was conducted in stainless-steel 20-l. fermentors with 10 l. of medium initially at pH 7.1 comprising the following nutrients:

TABLE I

Sources and Characteristics of Substrains of
X. campestris NRRL B-1459

| Substrain | Source | Colony size[a,b] | Xanthan Yield[c] | Quality[c] |
|---|---|---|---|---|
| B-1459A | Parent | | | |
| B-1459-S-29 | B-1459A | L | High | Good |
| B-1459-S-29 (old) | B-1459A | LS | Medium | Fair |
| B-1459A-IX | B-1459A | L | High | Good |
| B-1459L | B-1459A (old) | L | High | Good |
| B-1459S | B-1459A (old) | S | Low | Poor |
| B-1459-S-22 | B-1459A | L | High | Good |
| B-1459-S-39 | B-1459-S-22 | L | High | Good |
| B-1459-4L | B-1459S | L | High | Good |
| B-1459SP | B-1459S | S | Low | Poor |
| B-1459-4L (old) | B-1459S-4L | L | High | Fair |

[a]Streaked on yeast-malt agar.
[b]L = large; S = small; LS = large and small.
[c]Tested on productivity medium.

| | |
|---|---|
| D-glucose | 2.6% |
| $(NH_4)_2HPO_4$ | 0.15% |
| $K_2HPO_4$ | 0.25% |
| $MgSO_4$ | 0.01% |
| tap water | 96.99% |
| | 100.00% |

The fermentors containing a portion of the tap water were first sterilized by injecting steam into both the jacket and the medium and holding the temperature at 121° C. for 20 min. with agitation. The glucose was sterilized separately (in the fermentor) in tap water at pH 4.5 to avoid the browning reaction. The nitrogen source and salt mixture were sterilized apart from the ferementors at 121° C. for 40 min., and then added aseptically prior to inoculation. Air was passed through activated carbon filters which were also sterilized at 121° C. for 20 min. The fermentors were fitted with stainless-steel pipe spargers, a six-paddle stirrer set at the bottom, and a three-paddle stirrer set near the surface of the broth, both driven by variable speed-controlled (0 to 700 r.p.m.) heavy-duty motors. The air exhaust parts were fitted with water-cooled condensers to minimize evaporative loss of liquid volume during the fermentation. Controllers maintained the pH of the broths at a minimum of 6.8 using 1 M NaOH and foaming was controlled automatically using "Hodag FD-62" silicone diluted 1:10. In most instances, foaming did not occur. The media were inoculated by addition of the contents of two Fernbach flasks(10% v/v) from the second stage and incubation was conducted at 27° C. for 72 hours at an air flow rate of 1.5 vol./l./min. and a stirrer speed of 225 r.p.m. for the first 24 hours, and 300 r.p.m. for the remaining 48 hours.

A portion of the xanthan was isolated from each sample by first diluting 10 g. of whole culture fluid to 50 g. with distilled water and mixing thoroughly. The resultant suspension was centrifuged 30 min. at 20,000 r.p.m. in a Spinco Model L ultracentrifuge, rotor #21. Supernatant fluid was decanted and mixed with sufficient KCl to make a 1% solution. The gum was precipitated with 100 ml. of 95% ethanol and then recovered by sieving and washing with 20 ml. of 75% ethanol followed by 5 ml. of 95% ethanol. The products were dried overnight at room temperature and then 1-hours at 100° C. Polysaccharide yield was determined by weighing the dried product, and pyruvic acid content was determined by the enzymic method described by Jeanes et al. [USDA, ARS-NC-51 (1976)], herein incorporated by reference. Viscosities of crude culture fluids were measured at 25° C. with a Model LVF Brookfield viscometer at a constant speed of 30 r.p.m.

The results are reported in Table II. When employed within the limits of the invention, substrains S-4L from fresh stock cultures (less than 3 months old) consistently yielded polysaccharides having pyruvate contents on the order of 4%.

EXAMPLES 9–16

The procedure of Example 7 was repeated except that the levels of $(NH_4)_2HPO_4$ and $K_2HPO_4$ were varied as indicated in Table III, the glucose levels varied between 2.5% and 2.6%, and the air flow rate was 0.75 vol/l./min. The $(NH_4)_2HPO_4$ level in Example 9 and the total phosphate level in Example 10 were outside the scope of the invention, as evidenced by the relatively low pyruvic acid contents.

EXAMPLES 17–21

The procedure of Example 7 was repeated except that the nitrogen source, $K_2HPO_4$ level, and air flow rate were varied as indicated in Table IV, the glucose level was 2.5%, and the initial pH was 7.

EXAMPLES 22–29

The procedure of Example 7 was repeated except that the temperature and time of fermentation were varied as indicated in Table V and the pH was 7.

It is understood that the foregoing detailed description is given merely by way of illustration and that modification and variations may be made therein without departing from the spirit and scope of the invention.

TABLE II

Comparison of Substrains of X. campestris
NRRL B-1459 on Novel Media

| Example | Substrain | Culture broth Viscosity (cp.) | Xanthan (g./100 ml.) | Pyruvic acid in gum (g./100 g.) |
|---|---|---|---|---|
| 2 | L | 4960 | 1.1 | 3.7 |
| 3 | S | 3320 | 0.9 | 3.4 |
| 4 | SP | 2980 | 0.9 | 3.6 |
| 5 | S-39 | 3160 | 0.8 | 3.3 |
| 6 | S-29 | 2040 | 0.8 | 3.5 |
| 7 | S-4L | 6220 | 1.2 | 4.2 |
| 8 | S-4L (old) | 4620 | 1.1 | 3.4 |

TABLE III

Effect of (NH$_4$)$_2$HPO$_4$ and K$_2$HPO$_4$ on Xanthan Viscosity, Yield, and Pyruvic Acid

| Example | (NH$_4$)$_2$HPO$_4$ (g./100 ml.) | K$_2$HPO$_4$ (g./100 ml.) | Glucose (g./100 ml) | Culture broth Viscosity (cp.) | Xanthan (g./100 ml.) | Pyruvic acid in gum (g./100 g.) |
|---|---|---|---|---|---|---|
| 9  | 0.10 | 0    | 2.6 | 6700 | 1.30 | 2.4 |
| 10 | 0.15 | 0    | 2.5 | 4300 | 0.97 | 2.9 |
| 11 | 0.25 | 0    | 2.6 | 6380 | 1.27 | 3.8 |
| 12 | 0.35 | 0    | 2.6 | 6680 | 1.30 | 3.8 |
| 13 | 0.15 | 0.15 | 2.5 | 6820 | 1.32 | 3.6 |
| 14 | 0.25 | 0.10 | 2.6 | 5840 | 1.13 | 3.8 |
| 15 | 0.25 | 0.25 | 2.6 | 5860 | 1.22 | 4.1 |
| 16 | 0.25 | 0.50 | 2.5 | 5340 | 1.04 | 4.1 |

TABLE IV

Effect of Nitrogen Source on Xanthan Viscosity, Yield, and Pyruvic Acid

| Example | Nitrogen source$^a$ | Nitrogen source level (g./100 ml) | K$_2$HPO$_4$ level (g./100 ml) | Air flow rate (vol./l./min.) | Culture broth Viscosity (cp.) | Xanthan (g./100 ml.) | Pyruvic acid in gum (g./100 g.) |
|---|---|---|---|---|---|---|---|
| 17  | DDS          | 0.8  | 0.5  | 1.5  | 11120 | 1.7 | 2.9 |
| 18  | BYF          | 0.55 | 0.5  | 1.5  | 10740 | 1.5 | 2.7 |
| 19  | NaNO$_3$     | 0.09 | 0.5  | 1.5  | 6940  | 1.4 | 3.0 |
| 20A | NH$_4$NO$_3$ | 0.06 | 0.25 | 0.75 | 4680  | 0.8 | 2.1 |
| 20B | NH$_4$NO$_3$ | 0.15 | 0.25 | 0.75 | 4040  | 0.9 | 3.1 |
| 21  | (NH$_4$)$_2$HPO$_4$ | 0.25 | 0.5 | 1.5 | 6140 | 1.3 | 4.1 |

$^a$DDS = dried distillers' solubles; BYF = brewers' yeast autolysate.

TABLE V

Effect of Temperature and Time on Xanthan Viscosity, Yield, and Pyruvic Acid

| Example | Temperature (°C.) | Fermentation time (days) | Culture broth Viscosity (cp.) | Xanthan (g./100 ml.) | Pyruvic acid in biopolymer (g./100 g.) |
|---|---|---|---|---|---|
| 22 | 20 | 2 | 592  | 0.5 | 3.0 |
| 23 | 24 | 2 | 5460 | 1.1 | 3.7 |
| 24 | 27 | 2 | 6040 | 1.1 | 3.9 |
| 25 | 30 | 2 | 7880 | 1.3 | 2.9 |
| 26 | 20 | 3 | 4080 | 0.9 | 4.1 |
| 27 | 24 | 3 | 7020 | 1.3 | 3.6 |
| 28 | 27 | 3 | 7280 | 1.3 | 3.9 |
| 29 | 30 | 3 | 8380 | 1.4 | 3.0 |

We claim:

1. In a process for producing polysaccharides by fermentation of a carbohydrate-containing nutrient medium with the bacterium *Xanthomonas campestris*, wherein said bacterium is cultivated on said medium under conditions suitable for its growth, the improvement comprising:

a. providing (NH$_4$)$_2$HPO$_4$ as the primary nitrogen source in said nutritent medium at a level of at least 0.15 g./100 ml. of medium;

b. providing a total phosphate level in said nutrient medium of at least 0.25 g./100 ml. of medium; and c. recovering from said fermentation medium a polysaccharide isolated from residual solids in said medium wherein said polysaccharide has a pyruvic acid content of at least 3.3% by weight.

2. The process as defined in claim 1 wherein said (NH$_4$)$_2$HPO$_4$ is provided in an amount of 0.15–0.25 g./100 ml. of medium.

3. The process as defined in claim 1 wherein said nutrient medium comprises dipotassium phosphate or disodium phosphate.

* * * * *